(12) United States Patent
Iseri et al.

(10) Patent No.: US 7,550,114 B2
(45) Date of Patent: Jun. 23, 2009

(54) CELL OBSERVATION APPARATUS

(75) Inventors: Takafumi Iseri, Tokyo (JP); Teruaki Miyamura, Tokyo (JP); Junji Matsuda, Tokyo (JP); Shiro Kanegasaki, Tokyo (JP)

(73) Assignees: Hirata Corporation (JP); ECI, Inc. (JP)

( * ) Notice: Subject to any disclaimer, the term of this patent is extended or adjusted under 35 U.S.C. 154(b) by 79 days.

(21) Appl. No.: 10/572,801

(22) PCT Filed: Nov. 19, 2004

(86) PCT No.: PCT/JP2004/017299

§ 371 (c)(1),
(2), (4) Date: Mar. 22, 2006

(87) PCT Pub. No.: WO2005/054425

PCT Pub. Date: Jun. 16, 2005

(65) Prior Publication Data

US 2007/0054327 A1    Mar. 8, 2007

(30) Foreign Application Priority Data

Dec. 1, 2003   (JP)   ............................. 2003-400927

(51) Int. Cl.
*G01N 21/00* (2006.01)
(52) U.S. Cl. ................................... 422/82.05
(58) Field of Classification Search ............... 422/82.05
See application file for complete search history.

(56) References Cited

U.S. PATENT DOCUMENTS 5,521,699 A * 5/1996 Kosaka et al. .................. 356/73

(Continued)

FOREIGN PATENT DOCUMENTS

JP          05-276326          10/1993

(Continued)

OTHER PUBLICATIONS

Kanegasaki, S.; Nomura, Y.; Nitta, N.; Akiyama, S.; Tamatani, T.; Goshoh, Y.; Yashida, T.; Sato, T.; Kikuchi, Y. "A novel optical assay system for the quantitative measurement of chemotaxis," Journal of Immunological Methods, 2003, 282, pp. 1-11.*

*Primary Examiner*—Walter D Griffin
*Assistant Examiner*—Bobby Ramdhanie
(74) *Attorney, Agent, or Firm*—Bacon & Thomas, PLLC

(57) ABSTRACT

There is provided cell observation apparatus (10) comprising cell observation chamber (30) and optical observation means (70), the cell observation chamber (30) having, disposed thereinside, a pair of wells and a channel through which the wells communicate with each other so that cells of a cell suspension stocked in one of the pair of wells can react with a chemotaxis-factor-containing solution stocked in the other well and can move from the one well to the other well through the channel, the optical observation means (70) capable of optically observing the cells moving through the channel from outside of the cell observation chamber (30), wherein the cell observation chamber (30) with its part exposed from casing (20) is housed in the casing (20) and wherein the optical observation means (70) is housed in the casing (20) so that the optical axis thereof horizontally extends allow in the cell observation chamber (30). Thus, there can be obtained a cell observation apparatus that is compact, being easy in transfer and that has strikingly been improved with respect to handleability.

6 Claims, 11 Drawing Sheets

U.S. PATENT DOCUMENTS

| | | | |
|---|---|---|---|
| 5,744,366 A * | 4/1998 | Kricka et al. | 436/63 |
| 7,259,008 B2 * | 8/2007 | Kanegasaki et al. | 435/288.5 |
| 2003/0003570 A1 | 1/2003 | Kanegasaki et al. | |

FOREIGN PATENT DOCUMENTS

| | | | |
|---|---|---|---|
| JP | 11-118819 | | 4/1999 |
| JP | 2002-008249 | | 1/2002 |
| JP | 2002-159287 | | 6/2002 |
| JP | WO0246356 | * | 6/2002 |
| JP | 2003-088357 | | 3/2003 |
| JP | 2003-180336 | | 7/2003 |
| JP | 2003-330093 | | 11/2003 |

* cited by examiner

CELL OBSERVATION APPARATUS

BACKGROUND OF THE INVENTION

1. Field of the Invention

The present invention relates to a cell observation apparatus, and specifically to a small-sized cell observation apparatus with improved operationality used for: for example, determining whether or not cells move in a certain direction by themselves; observing a state where cells move in a certain direction by themselves; and measuring the number of cells that have moved in a certain direction by themselves. The apparatus can be used also for isolating cells that move in a certain direction by themselves.

2. Description of the Prior Art

There have conventionally been proposed and marketed various kinds of cell observation apparatuses. In particular, there has been proposed on apparatus, as described in Japanese Patent Laid-Open Publication No. 2002-159287 and Japanese Patent Laid-Open Publication No. 2003-180336, adapted to be capable of observing and quantitating the self-based movement of cells precisely and easily using a few cell samples to detect the chemotaxis of the cells due to chemotactic factor or the chemotaxis inhibition of the cells due to chemotactic factor inhibitor. In this apparatus, it is also possible to isolate the cells utilizing the chemotaxis of the cells.

In the cell observation apparatus described in the foregoing publication, a cell observation chamber portion is arranged as follows.

As shown in FIG. 18, the cell observation chamber 00 comprises: a circular shallow dish-shaped bottom support body 01 with a window 01c for observing the movement of cells provided in the center of the bottom part thereof, a glass substrate 08 adapted to be placed on the bottom part 01a of the bottom support body 01; a dish-shaped intermediate support body 02 adapted to be attached to the bottom support body 01 to press and fix the glass substrate 08 from above onto the bottom part 01a by connecting a cover 04 to be described hereinafter to the bottom support body 01 with screws; a substrate 07 and a packing member 010 adapted to be fitted into a rectangular opening portion 02c that is formed in the center of the bottom part of the intermediate support body 02 to be fixed onto the glass substrate 08; a block body 09 adapted to be fitted into the central recessed portion of the intermediate support body 02 to press and fix the substrate 07 onto the glass substrate 08 through the packing member 010 using pressing screws not shown in the figure; and a cover 04 adapted to be attached to the bottom support body 01 through a screw connection to press and fix the block body 09 from above to the intermediate support body 02. The substrate 07 is made of silicon single-crystal material.

The connection between the bottom support body 01 and the intermediate support body 02 is to be made by screwing a male thread 02d formed in the outer peripheral surface of the body part of the intermediate support body 02 into a female thread 01d formed in the inner peripheral surface of the body part of the bottom support body 01 and by a screw connection between the bottom support body 01 and the cover 04. The screw connection between the bottom support body 01 and the cover 04 is to be made by screwing a male thread 01e formed in the outer peripheral surface of the bottom support body 01 into a female thread 04a formed in the inner peripheral surface of the sleeve part of the cover 04. The intermediate support body 02 is to be positioned on the bottom support body 01 by inserting guide pins (not shown in the figure) disposed on the upper surface of the body part of the bottom support body 01 into guide pin receiving holes 02f formed in the lower surface of the flange part 02b of the intermediate support body 02. Also, the block body 09 is to be positioned in the intermediate support body 02 by inserting guide pins 013 disposed on the bottom surface of the intermediate support body 02 into guide pin receiving holes 09a formed in the bottom surface of the block body 09.

Then, in a state where the above components are assembled integrally and used, at least a pair of wells and a flow path for communicating of these wells are to be formed between the substrate 07 and the glass substrate 08. One of these wells is to be provided with cell suspension, while the other thereof is to be provided with chemotactic factor containing solution, so that cells move from one to the other of the wells through the flow path in response to the chemotactic factor. A microscopic observation is to be carried out through the window 01c to observe the state and to measure the number of moving cells.

The injection of cell suspension and chemotactic factor containing solution into one and the other wells that are formed between the substrate 07 and the glass substrate 08 is to be performed using a micropipette through specialized through holes formed, respectively, in the block body 09, the packing member 010, and the substrate 07. After assembling the bottom support body 01, the intermediate support body 02, and the cover 04, an O-ring 011 is to be interposed between the intermediate support body 02 and the glass substrate 08 so that no solution filling the bottom support body 01 leaks. On the other hand, the packing member 010 is also provided between the substrate 07 and the block body 09 so as to be useful in preventing each solution from leaking from the wells and the flow path for communicating of the wells.

Meanwhile, in order to observe the state of cells that move from one to the other of the wells through the flow path and to measure the number of moving cells precisely, it is necessary to control the temperature of the cell suspension and the chemotactic factor containing solution or the mixture containing these solutions filling these sections so as to be suitable for the activity of the cells. Also when it is demanded that the reaction of the cells due to temperature change be measured and analyzed more precisely, it is necessary to control the temperature of the solutions. For these reasons, in this apparatus, the cell observation chamber 00 is adapted to be placed on a heating section composed of heating elements not shown in the figure, and a temperature control device is used to heat these solutions indirectly through the wall of the bottom support body 01 to control these solutions to be a desired temperature while controlling the heating section to be a predetermined temperature.

Meanwhile, when observing a state where chemotactic cells move and measuring the number of moving cells using thus arranged cell observation chamber 00 through the window 01c in a microscopic observation, an optical axis in the optical system of the microscope is kept vertical, which causes the overall size of the cell observation apparatus with the cell observation chamber 00 and the microscope facility, etc. incorporated therein to be increased and therefore the movement thereof to be made complicated, resulting in that there is still room for improvement in operationality.

Patent Document 1: Japanese Patent Laid-Open Publication No. 2002-159287

Patent Document 2: Japanese Patent Laid-Open Publication No. 2003-088357

Patent Document 3: Japanese Patent Laid-Open Publication No. 2003-180336

Patent Document 4: Japanese Patent Laid-Open Publication No. Hei 11-118819

SUMMARY OF THE INVENTION

The present invention has been made to solve the above-described problems of the conventional cell observation apparatus, and an object thereof is to provide a small-sized and easily movable cell observation apparatus with significantly improved operationality.

In accordance with the present invention, the foregoing object can be achieved with the following cell observation apparatus.

That is, the cell observation apparatus comprises a cell observation chamber and optical observation means, the cell observation chamber comprising therein a pair of wells and a flow path for communicating of the wells and being arranged in such a manner that cells in cell suspension stored in one of the pair of wells can react with chemotactic factor containing solution stored in the other of the wells to move from one to the other of the wells through the flow path, and the optical observation means being adapted to be capable of observing the cells moving through the flow path optically from outside the cell observation chamber, wherein the cell observation chamber is housed in a casing of the cell observation apparatus in such a manner that the side of providing or removing the solutions thereof is partially exposed from the casing, and wherein the optical observation means is housed in the casing below the cell observation chamber in such a manner that the optical axis thereof extends horizontally.

In accordance with the cell observation apparatus, since the optical observation means is housed in the casing below the cell observation chamber in such a manner that the optical axis thereof extends horizontally, the overall height of the casing can be saved considerably, which can reduce the size and weight of the cell observation apparatus to be movable easily. Also, the apparatus can be operated easily, resulting in a significant improvement in operationality.

In a preferred embodiment, the optical observation means comprises an optical system on a stage movable in an XY two-dimensional plane, the system consisting of an objective lens, a plurality of reflecting mirrors, a half mirror, a light source, and a camera, the objective lens being arranged near a window provided in the cell observation chamber so as to be capable of observing the cells moving through the flow path, and the light source being adapted to illuminate the cells moving through the flow path through the optical system to allow the camera to image the cells visibly.

This allows the optical observation means to move and align the objective lens to a position under the flow path through which cells to be observed move and to magnify the cells, so that the camera can take a visible image of the cells and that a state where the cells move can be observed and the number of the cells can be measured using the image, which facilitates the cell observing operation significantly. Since there is also provided the half mirror, it is possible to change the angle of the optical axis randomly, which can further reduce the size of the cell observation apparatus.

In another preferred embodiment, the cell observation apparatus further comprises temperature control means, the temperature control means having means for controlling the atmosphere in the casing and the main body of the casing to be a predetermined temperature, whereby the temperature change of each part housed in the casing and constituting the cell observation apparatus can have a regular impact on the chemotaxis of cells, which can further improve the accuracy in observing the cells.

As described heretofore, in accordance with the present invention, it is possible to reduce the size and weight of the cell observation apparatus to be movable easily, and also the apparatus can be operated easily, resulting in a significant improvement in operationality.

Also, the optical observation means can magnify cells moving through the flow path to a desired size to allow the camera to image the cells visibly, and it is also possible to use a personal computer to, for example, operate the cell observation apparatus, observe the state of the cells, and hold, process, and analyze data, which facilitates the cell observing operation significantly and also enables the operation to be performed on a desk.

Further, the cell observation apparatus has the temperature control means for controlling the atmosphere in the casing and the main body of the casing to be a predetermined temperature, whereby the temperature change of each part housed in the casing and constituting the cell observation apparatus and of the main body of the casing can have a regular impact on the chemotaxis of cells, which can improve the accuracy in observing the cells.

DESCRIPTION OF THE PREFERRED EMBODIMENTS

Figure 1:
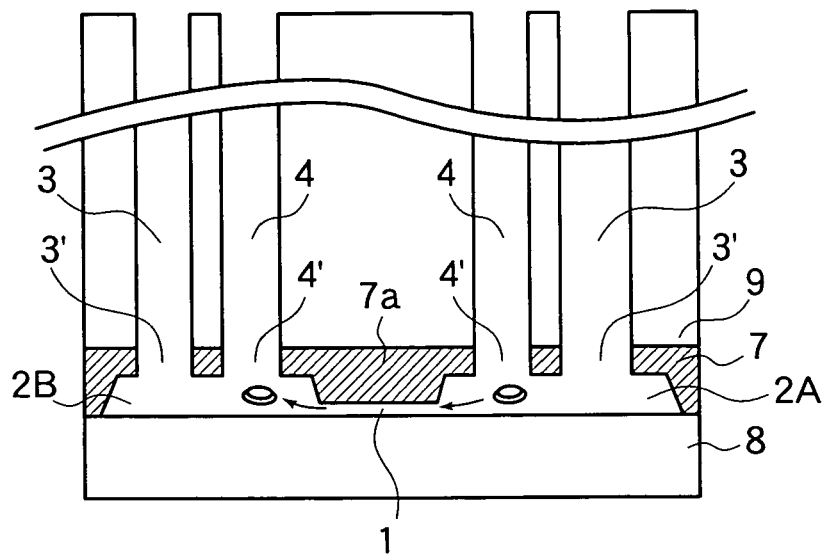
FIG. 1 is a side view of a cell observation chamber according to an embodiment of the present disclosure.

In a cell observation apparatus comprising a cell observation chamber and optical observation means, the cell observation chamber comprising therein a pair of wells and a flow path for communicating of the wells and being arranged in such a manner that cells in cell suspension stored in one of the pair of wells can react with chemotactic factor containing solution stored in the other of the wells to move from one to the other of the wells through the flow path, and the optical observation means being adapted to be capable of observing the cells moving through the flow path optically from outside the cell observation chamber, it is arranged that the cell observation chamber is housed in a casing of the cell observation apparatus in such a manner that the side of providing or removing the solutions thereof is partially exposed from the casing, and that the optical observation means is housed in the casing below the cell observation chamber in such a manner that the optical axis thereof extends horizontally.

It is arranged that the optical observation means comprises an optical system on a stage movable in an XY two-dimensional plane, the system consisting of an objective lens, a plurality of reflecting mirrors, a half mirror, a light source, and a camera, the objective lens being arranged near a window provided in the cell observation chamber so as to be capable of observing the cells moving through the flow path, and the light source being adapted to illuminate the cells moving through the flow path through the optical system to allow the camera to image the cells visibly.

It is arranged that the cell observation apparatus further comprises temperature control means, the temperature control means having a function of controlling the solutions filling the wells and the flow path to be a predetermined temperature and of controlling the atmosphere in the casing to be a predetermined temperature.

It is arranged that on the upper surface of the casing is placed a personal computer capable of holding a program for temperature control in the temperature control means and cell observation data, etc., processing the data, and displaying desired data on a display, while the lower surface of the casing is fitted with tilt adjustment means for adjusting the tilt of the casing.

Next will be described an embodiment of the present invention.

The principle of the operation of a cell observation apparatus according to the present invention will first be described.

In a cell observation chamber incorporated in the cell observation apparatus, a plurality of wells are connected and communicate with each other through a flow path, in each well being provided two pipes: one is for injecting or removing samples, and the other is for preventing the pressure in the well from increasing or decreasing due to the operation of injecting or removing the samples. These pipes may be formed by through holes formed in a block. It is here noted that the flow path is a part for communicating of two wells, that is, a channel through which cells pass when moving from one to the other of the wells. In accordance with the apparatus, since the liquid flow toward the opposite wells in the flow path is unlikely to occur when injecting or removing samples, there is no possibility that the liquid in the wells provided on both ends of the flow path intermingles with each other, whereby it is possible to detect the case where cells mainly move based only on the effect of chemotactic factor.

Figure 2:
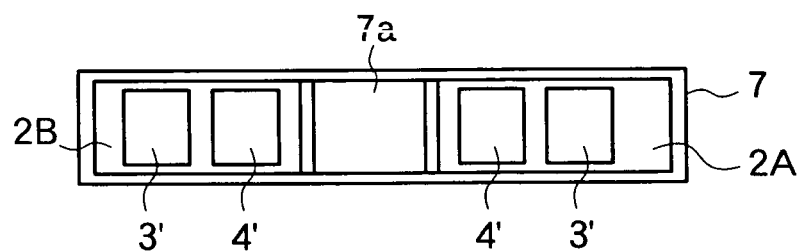
FIG. 2 is a bottom view of the cell observation chamber according to FIG. 1.

To describe the principle based on the accompanying drawings, in FIGS. 1 and 2, the numeral 1 indicates a flow path, and the numeral 2 indicates wells for storing samples such as cell suspension and specimen solution, consisting of a pair of wells 2A and 2B. These samples are provided or removed to/from the wells 2 through the through holes 3 formed in the block body 9 using a micropipette, etc. When one well 2A of the wells 2 is provided with the cell suspension, cells try to move toward the other well 2B and pass through the flow path 1 if the specimen solution put in the well 2B contains chemotactic factor (chemotactic factor containing solution).

When providing the cell suspension, one sample, to the well 2A through the through hole 3 using a micropipette, etc., there is a possibility that cells move toward the well 2B provided on the opposite side through the flow path 1 due to the pressure of the liquid injected. This situation, if occurred, causes confusion about determining whether or not the movement of the cells is due to the chemotactic factor contained in the specimen, and in the case of aiming at isolating cell, causes desired cells to intermingle with other cells, which makes it impossible to achieve the purpose. In order to solve the problem, this apparatus is arranged in such a manner that an injection pressure to be applied to the through hole 3 is released toward the through hole 4 to prevent cells from being flowed forcibly toward the flow path 1.

Also, when providing the specimen solution to the well 2B through the through hole 3 using a micropipette, etc., there is a possibility that the specimen solution enters the well 2A provided on the opposite side through the flow path 1 due to the pressure of the liquid injected to intermingle with the cell suspension, and therefore the phenomenon that cells pass through the flow path 1 due to the chemotaxis thereof may be confused or disturbed. In order to prevent such a situation from occurring, a through hole 4 is also provided in the well 2B for storing the specimen.

Thus providing the through holes 4 that communicate with the through holes 3 for injecting the samples therethrough can minimize the horizontal impact of the liquid pressure and thereby can determine whether or not the specimen solution has chemotaxis more precisely. The effect of reducing pressure difference using the through holes 4 is also effective in reducing pressure reduction when removing samples such as cells from the wells, which therefore makes it easy to remove the samples.

To describe the case of injecting samples into the wells 2 in this cell observation chamber with reference to FIG. 1, the wells 2A and 2B and the flow path 1 are preliminarily filled with cell isotonic solution, and then approximately the same quantity of cell suspension and chemotactic factor containing solution is injected, respectively, through the through hole 3 of the well 2A and the through hole 3 of the well 2B. This allows the pressure increase when injecting the samples to be reduced by the through holes 4.

Figure 3:
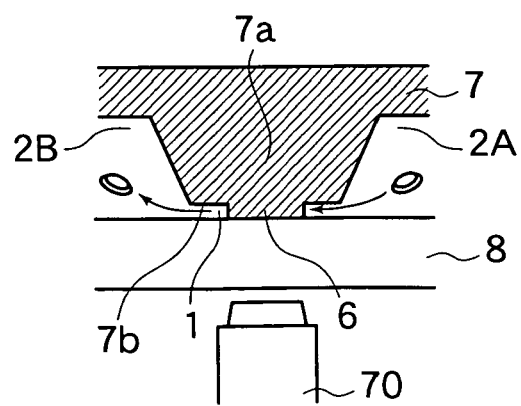
FIG. 3 is an enlarged partial view of the cell observation chamber according to FIGS. 1 and 2, and including the optical observation means.
Figure 4:
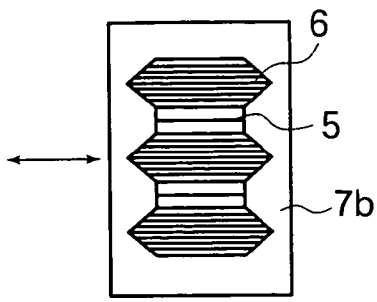
FIGS. 4 and 5 show a front and an expanded side view of the grooves forming the barrier.
Figure 5:
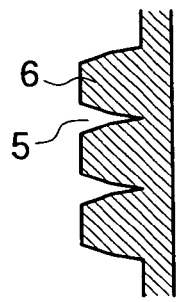

As shown in FIGS. 3 to 5, the flow path 1 is composed of one or a plurality of, for example about 100, grooves 5 formed in a barrier 6 along the direction or the opposite direction from the well 2A toward the well 2B, the barrier 6 running in the direction perpendicular to the direction or the opposite direction from the well 2A toward the well 2B. These grooves 5 are formed at a width in accordance with the diameter of cells or the deformability thereof. Thus providing the grooves 5 makes it possible to observe the cells at individual level and also to isolate the cells into desired classes. It is noted that the numeral 7a in FIGS. 1 to 3 indicates a bank formed between the wells 2A and 2B, while the numeral 7b in FIGS. 3 and 4 indicates a terrace formed on the bank 7a. The terrace 7b is a flat portion surrounding the barrier 6.

An observation of a state where cells move through the flow path 1 and a measurement of the number of cells that currently pass or have passed through the flow path 1 are to be made by setting observation means, for example, a microscope or optical observation means 70 (refer to FIG. 17) having a structure achieved by combining a microscope with a video camera or a CCD camera (Charge-Coupled Device camera) as will be described hereinafter, in such a manner that the observation means faces the flow path 1 through a glass substrate 8 as shown in FIG. 3. Using thus arranged optical observation means 70 makes it possible to record the progress of the cell movement automatically.

Defining such an apparatus as mentioned above, in which the wells 2A and 2B with the through holes 3 and 4 provided respectively therein are communicated with each other through the flow path 1, as one unit and integrating a plurality of units makes it possible to construct an apparatus whereby the movement (chemotaxis) of cells can be detected and chemotactic cells can be isolated at the same time for other kinds of specimens or other kinds of cells. Since the size of such an apparatus is wholly reduced, it is possible to treat samples at a small quantity. In addition, the treatment can be automated easily with a program control system for the injection/removal quantity of the liquid.

Such a unit as mentioned above, in which the wells 2A and 2B with the through holes 3 and 4 provided respectively therein are communicated with each other through the flow path 1, is actually manufactured as follows.

The inner shape of the wells 2A and 2B and the flow path 1 can be formed by applying a known technique for manufacturing an integrated circuit onto the surface of a substrate 7 made of silicon single-crystal material. Arranging the substrate 7 with a concavo-convex shape obtained by thus transferring the inner shape of the wells 2A and 2B and the flow path 1 thereto engraved on the surface thereof to face and overlap the glass substrate 8 causes the wells 2A and 2B and the flow path 1 to be formed between the substrates 7 and 8.

In the substrate 7, through holes 3' for guiding cell suspension or chemotactic factor containing solution therethrough are also formed correspondingly to the respective wells 2A and 2B in a vertically penetrating manner, and through holes 4' for reducing pressure increase or pressure reduction that occurs when injecting or removing the solutions into/from the wells 2A and 2B are formed in pairs with the respective through holes 3' in a vertically penetrating manner. These pairs of through holes 3' and 4' are communicated with each other through the well 2A or 2B and communicate with the respective through holes 3 and 4 that are formed in the block body 9 in a vertically penetrating manner. It is noted that there is actually interposed a packing between the substrate 7 and the block body 9 so as to seal the liquid therebetween.

Next will be described in detail the cell observation chamber according to the present embodiment in which a plurality of such units as mentioned above, in which the wells 2A and 2B with the through holes 3' and 4' provided respectively therein are communicated with each other through the flow path 1, are incorporated.

The outline of the overall structure of the cell observation apparatus to which the cell observation chamber according to the present embodiment is applied will first be described.

Figure 6:
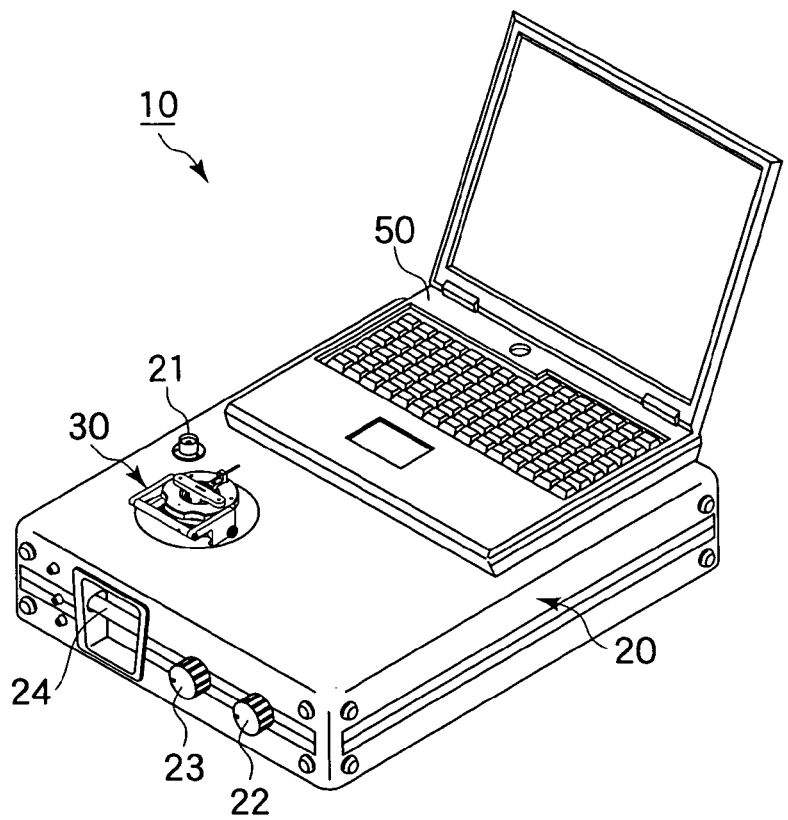
FIG. 6 is a perspective view of a cell observation apparatus according to an embodiment of the present disclosure.

As shown in FIG. 6, in the cell observation apparatus 10 to which the cell observation chamber 30 according to the present embodiment is applied, the cell observation chamber 30 is housed in such a manner as to be partially exposed on the upper surface of a relatively low casing 20 having a rectangular parallelepiped shape. Also, a laptop computer 50 is installed or placed detachably on the upper surface of the casing 20, and the laptop computer 50 is adapted to operate to, for example, give instructions to a temperature control section for solutions containing cell suspension, etc. and analyze, record, and display temperature data and/or cell observation data. The displaying includes displaying an image of an actual cell movement.

Since a level 21 is additionally attached to the upper surface of the casing 20, it is possible to monitor the evenness of the apparatus 10 constantly. Then, if the apparatus is out of the horizontal position, it is possible to restore the evenness by adjusting the screwing amount of tilt adjustment means 27 (refer to FIG. 16) attached to the lower surface of the casing 20. Also, variously adjusting the screwing amount of the tilt adjustment means 27 allows the angle of the apparatus 10 to be changed variously, which makes it possible to observe the impact of the gravity on the chemotaxis of cells.

A brightness (light intensity) adjustment knob 22 for a cell observation image in the optical observation means 70, a position adjustment knob 23 for the optical observation means 70, and a focal point adjustment knob 24, etc. are attached to the front surface of the casing 20 in this order from the lower right to the upper left in FIG. 6. Since an optical axis of the optical observation means 70 is arranged in such a manner as to extend horizontally in the casing 20 as will be described hereinafter, it is possible to reduce the height of the casing 20 and therefore the apparatus 10, which makes it possible to perform the operation of detecting cell chemotaxis, isolating chemotactic cells, and measuring the number of cells in a sitting posture using the apparatus 10 placed on a desk, resulting in a significant improvement in operationality. The arrangement of each device in the casing 20 will hereinafter be described in detail.

The cell observation chamber 30 is arranged as follows.

Figure 7:
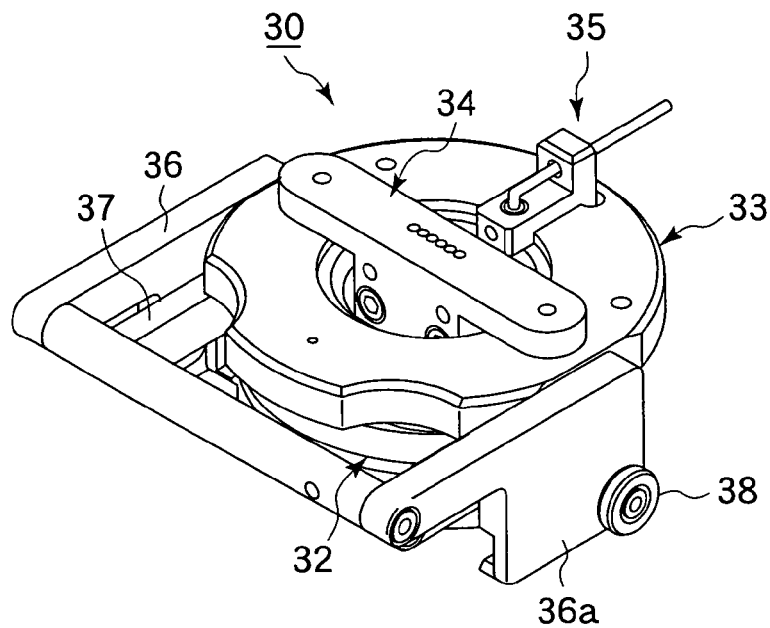
FIG. 7 is a an overall perspective view of a cell observation chamber according to an embodiment of the present disclosure.
Figure 8:
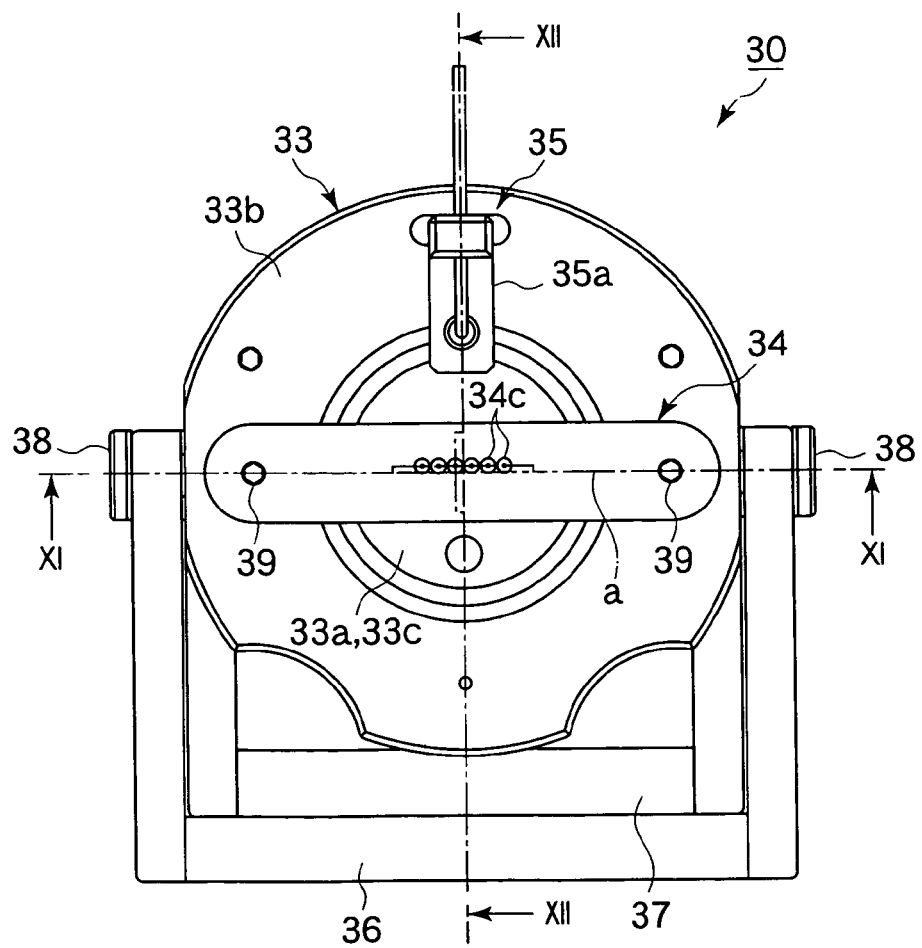
FIG. 8 is a plan view of the chamber shown in FIG. 7.
Figure 9:
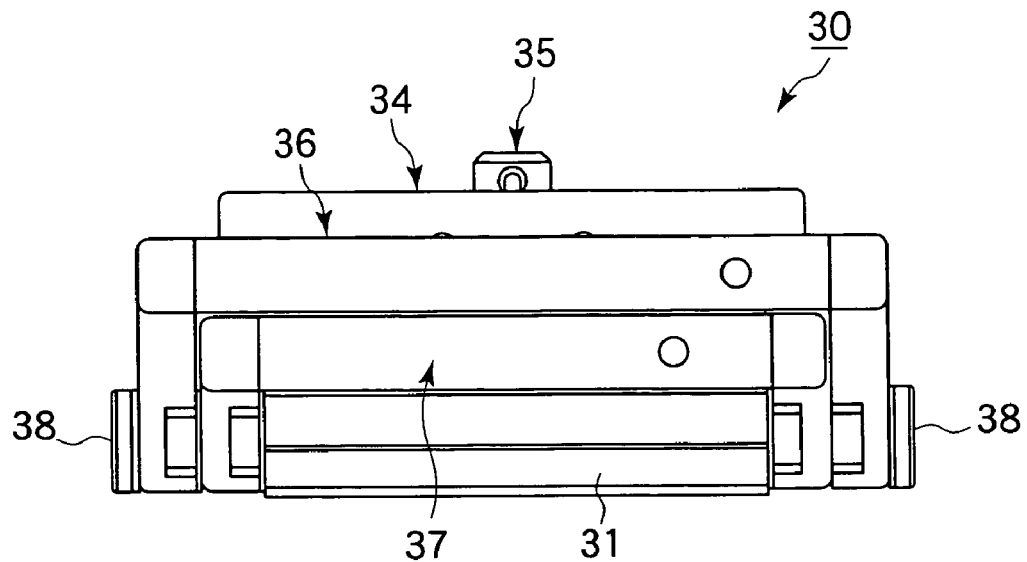
FIG. 9 is a front elevational view of the chamber shown in FIG. 7.
Figure 10:
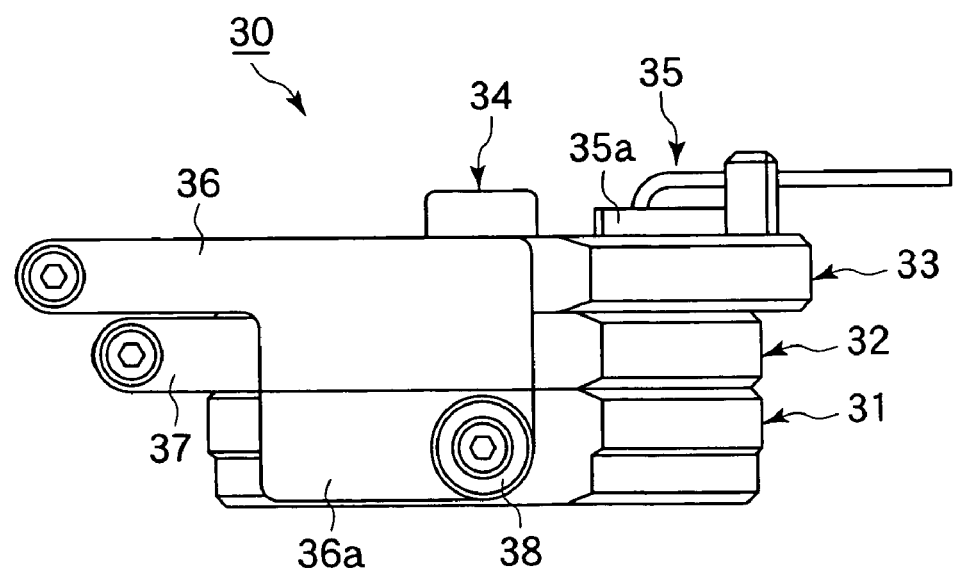
FIG. 10 is a right side elevational view of the chamber shown in FIG. 7.
Figure 11:
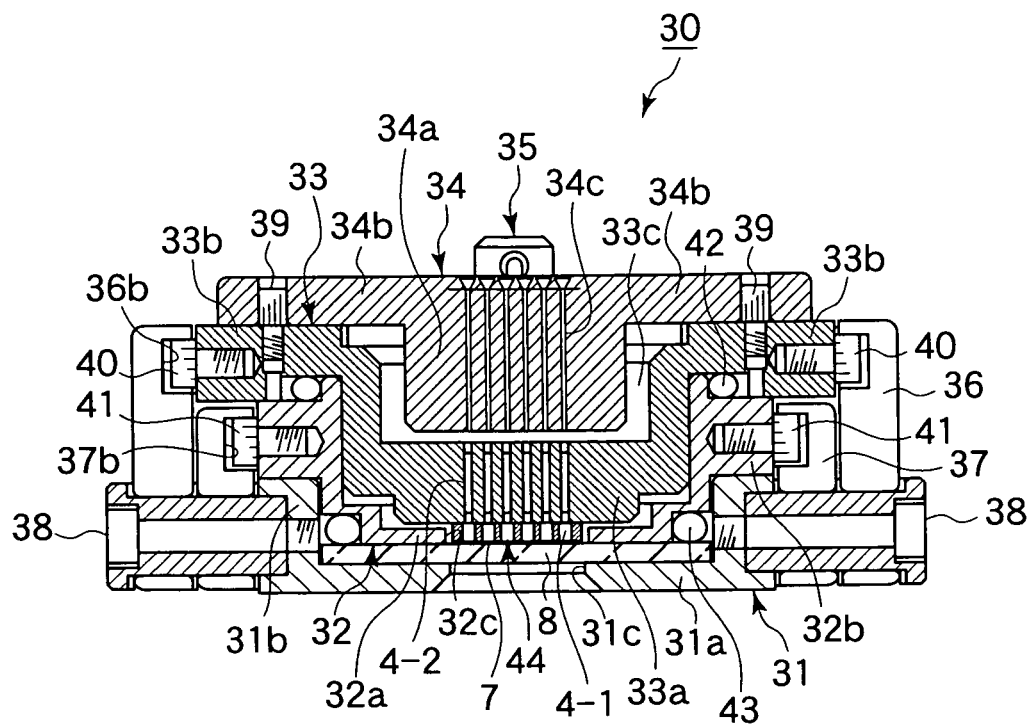
FIG. 11 is a cross-sectional view taken along line XI-XI in FIG. 8.
Figure 12:
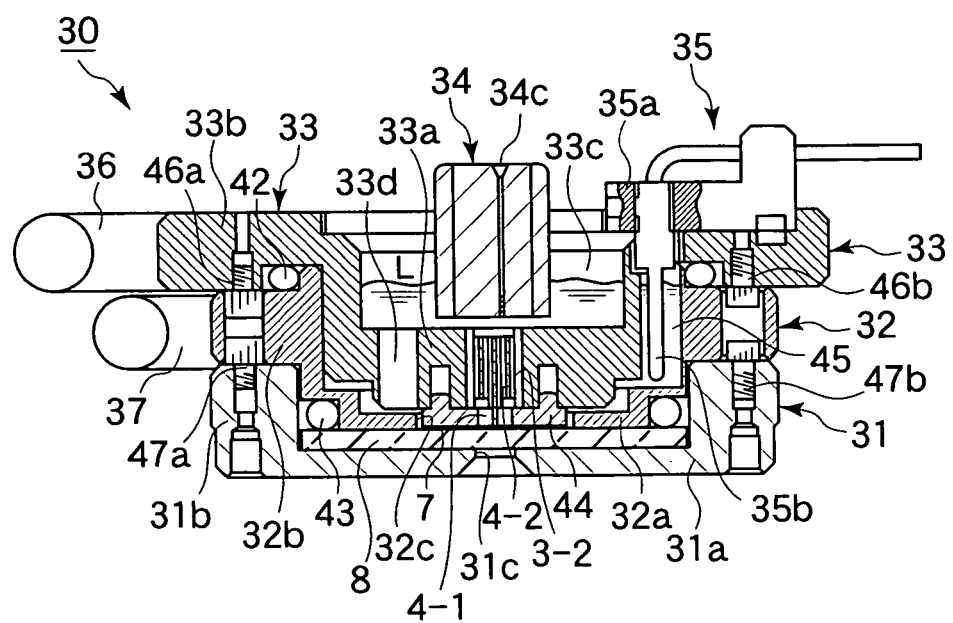
FIG. 12 is a cross-sectional view taken along line XII-XII in FIG. 8.
Figure 13:
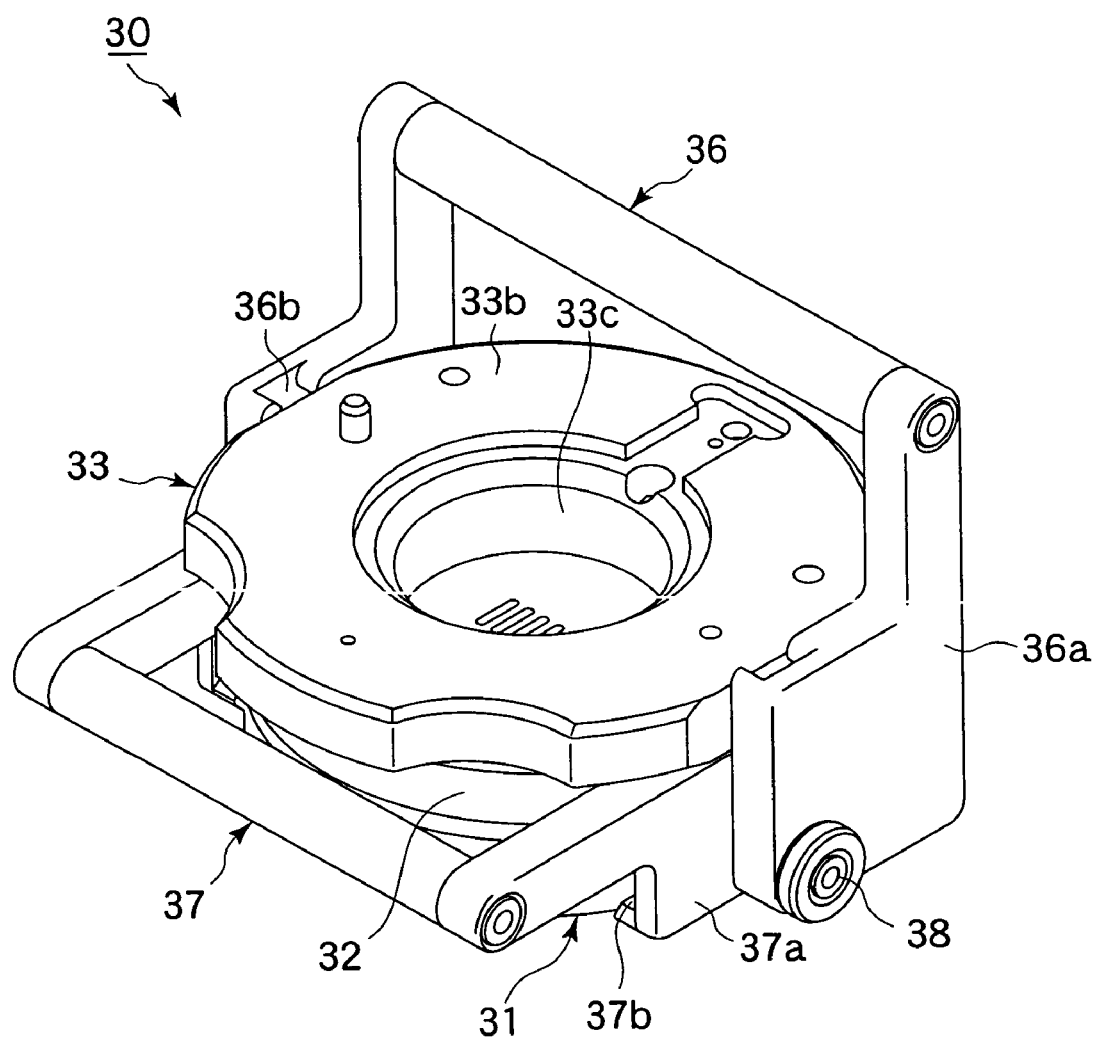
FIG. 13 is a partially disassembled perspective view of the chamber shown in FIG. 7.
Figure 14:
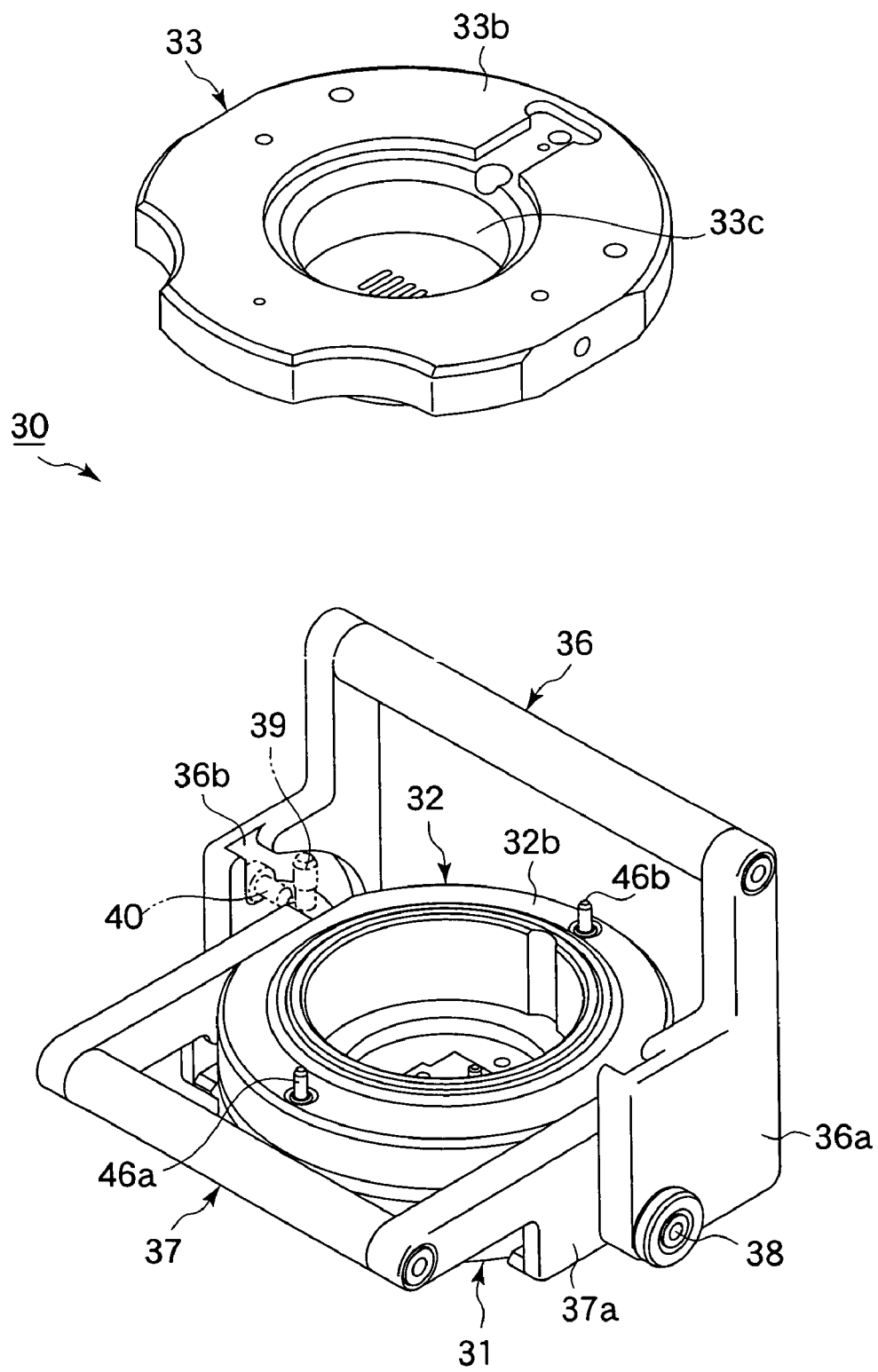
FIG. 14 is a further disassembled perspective view of the chamber shown in FIG. 7.

FIG. 7 is an overall perspective view of the cell observation chamber 30; FIG. 8 is a plan view of the chamber; FIG. 9 is a front elevational view of the chamber; FIG. 10 is a right side elevational view of the chamber; FIG. 11 is a cross-sectional view indicated by the arrow line XI-XI in FIG. 8; FIG. 12 is a cross-sectional view indicated by the arrow line XII-XII in FIG. 8; FIG. 13 is a partially disassembled perspective view of the cell observation chamber 30; and FIG. 14 is a further disassembled perspective view of the chamber.

As shown in FIGS. 7 to 10, 13, and 14, the arrangement of the cell observation chamber 30 will be understood as follows based on the appearance thereof and a partially disassembled state achieved by a simple rotational operation of cam control levers 36 and 37 to be described hereinafter. That is, onto a circular dish-shaped bottom support body 31 that is arranged in the lowest part is attached an intermediate support body 32 having also a circular dish shape; onto the intermediate support body 32 is attached a cover block body 33 having also a circular dish shape with the relatively thick bottom part 33a and the relatively wide outer peripheral flange part 33b; onto the cover block body 33 is attached a guide block body 34 across the central recessed portion 33c of the cover block body 33 in such a manner that the central enlarged portion 34a thereof is sunk into the central recessed portion 33c; and on the upper surface of the cover block body 33 is seated a pedestal part 35a of a temperature sensor 35.

Figure 18:
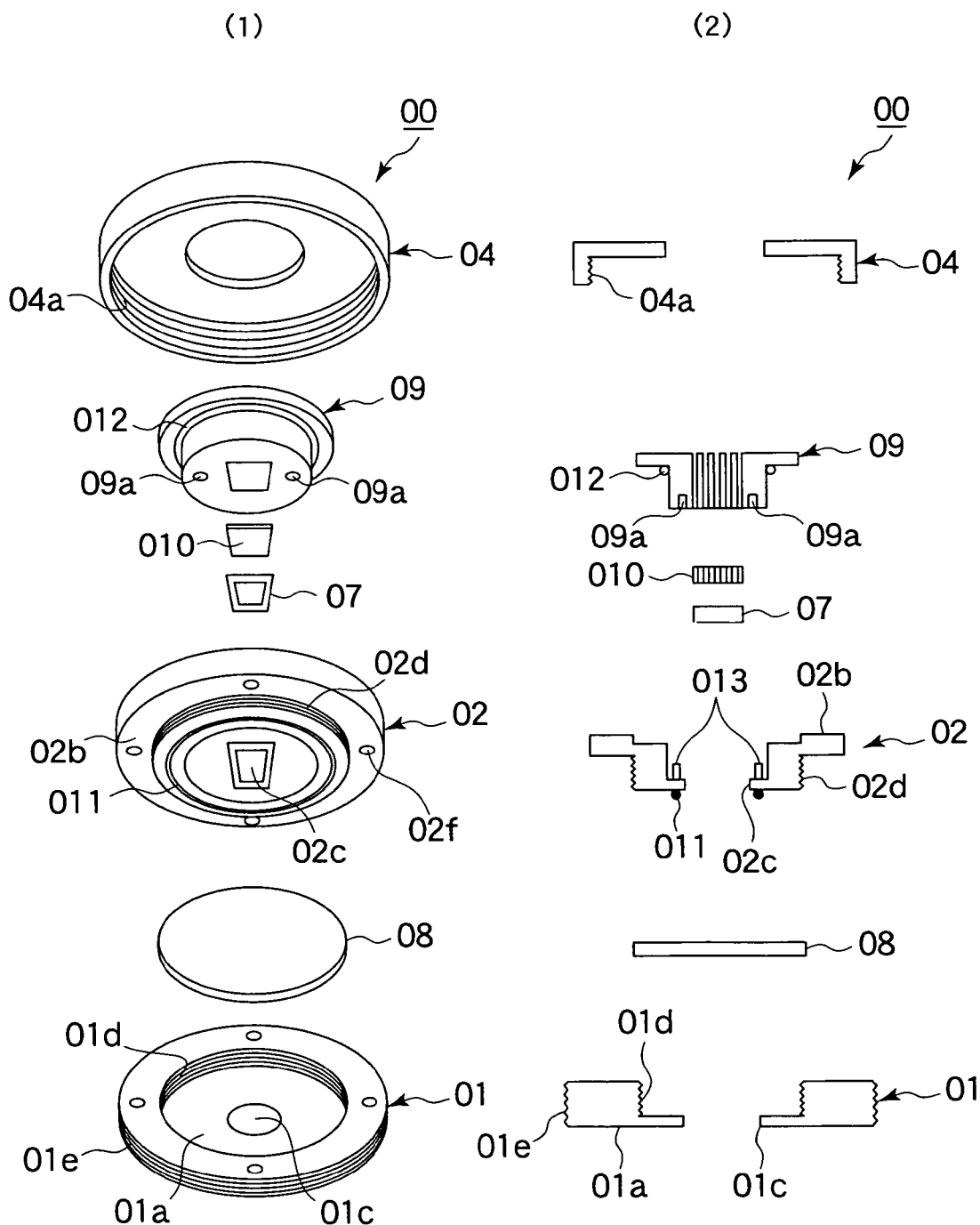
FIGS. 18(1) and (2) are exploded perspective and side views of a cell observation chamber according to an embodiment of the present disclosure.

Then, rotating the cam control lever 36 causes the cover block body 33 to be brought into pressurized contact with the intermediate support body 32 from above, which causes the intermediate support body 32 to be brought into pressurized contact with the bottom support body 31 from above, so that the cover block body 33 is finally to be attached to the bottom support body 31. Also, rotating the cam control lever 37 causes the intermediate support body 32 to be brought into pressurized contact with the bottom support body 31 from above and to be attached thereto. It is noted that in an actual attachment order, the intermediate support body 32 is first attached to the bottom support body 31, and the cover block body 33 is then attached to the bottom support body 31. In the case of a disassembling operation, the operation is to be performed in the reverse order. The cover block body 33 corresponds to one obtained by combining the block body 09 and the cover 04 in the conventional cell observation chamber 00 (refer to FIG. 18).

The cam control levers 36 and 37 each have a U shape when viewed from above, and the end portions 36a and 37a of the both leg parts thereof exist on the outer peripheral surface of the body part 31b of the circular dish-shaped bottom support body 31 to be supported rotatably around a pair of support shafts 38 that are implanted symmetrically with respect to the axial center of the body part. Also, the end portions 36a and 37a of the both leg parts are enlarged into a rectangular shape when viewed from front, in the inner surface of which being formed curved cam grooves 36b and 37b, respectively, for the cam control levers 36 and 37 (refer to FIGS. 13 and 14).

On the outer peripheral surface of the outer peripheral flange part 33b of the circular dish-shaped cover block body 33, there are implanted pins 40 symmetrically with respect to the axial center of the flange part (refer to FIGS. 14 and 11). The pins 40 are fitted into the cam grooves 36b of the cam control lever 36 so as to move within the cam grooves 36b in a sliding manner when the cam control lever 36 is rotated. This causes the lower surface of the outer peripheral flange part 33b of the cover block body 33 to come close to and to be brought into contact with the upper surface of the outer peripheral flange part 32b of the intermediate support body 32 from above, and then to be attached to the bottom support body 31. Also, rotating the cam control lever 36 reversely causes the cover block body 33 to be detached from the bottom support body 31. Between the outer peripheral flange part 33b of the cover block body 33 and the outer peripheral flange part 32b of the intermediate support body 32, there is interposed an O-ring 42 for preventing medium from leaking from an inner space to be formed between the cover block body 33 and the intermediate support body 32 when the cover block body 33 is attached to the intermediate support body 32.

Similarly, on the outer peripheral surface of the outer peripheral flange part 32b of the circular dish-shaped intermediate support body 32, there are implanted pins 41 symmetrically with respect to the axial center of the flange part (refer to FIG. 11). The pins 41 are fitted into the cam grooves 37b of the cam control lever 37 so as to move within the cam grooves 37b in a sliding manner when the cam control lever 37 is rotated. This causes the lower surface of the outer peripheral flange part 32b of the intermediate support body 32 to come close to and to be brought into contact with the upper surface of the body part 31b of the bottom support body 31 from above, and to be attached to the bottom support body 31 firmly. Also, rotating the cam control lever 37 reversely causes the intermediate support body 32 to be detached from the bottom support body 31.

In the central enlarged portion 34a of the guide block body 34, there are formed six narrow through holes 34c in a vertically penetrating manner aligned in the longitudinal direction of the guide block body 34. When an operator inserts or withdraws the needlepoint of a micropipette (not shown in the figure) carrying a sample such as cell suspension or specimen solution into/from the chamber 30, these through holes 34c are useful in guiding the needlepoint of the micropipette and in guiding the solution discharged from the micropipette to the well to be described hereinafter (this well is identical with one of the foregoing pair of wells 2A and 2B (FIG. 1)). The position where the six through holes 34c are aligned is displaced slightly toward one side of a centerline "a" dividing the guide block body 34 into two sections in the width direction when viewed from above (refer to FIG. 8).

The guide block body 34 is positioned and attached onto the flange part 33b detachably with pins 39 penetrating through arm parts 34b and 34b on either side of the central enlarged portion 34a and the flange part 33b of the cover block body 33. Therefore, after the guide block body 34 is detached from the cover block body 33 and rotated by 180 degrees so that the positions of the arm parts 34b and 34b on either side are switched with each other, the guide block body 34 can be attached again onto the flange part 33b of the cover block body 33 detachably by being positioned using the pins 39 similarly before the switching. In this case, the position where the six through holes 34c are aligned is symmetrical to the alignment position before the switching with respect to the centerline "a".

In order to position the cover block body 33 and the intermediate support body 32 relatively in the circumferential direction, a pair of positioning pins 46a and 46b penetrate through holes formed respectively therefor across the cover block body 33 and the intermediate support body 32 (refer to FIGS. 12 and 14). Similarly, in order to position the intermediate support body 32 and the bottom support body 31 relatively in the circumferential direction, a pair of positioning pins 47a and 47b penetrate through holes formed respectively therefor across the intermediate support body 32 and the bottom support body 31 (refer to FIG. 12). The pins 46a and 46b and the pins 47a and 47b have their respective different diameters to fulfill a function of preventing an assembling error in an assembling operation from occurring.

Next will be described the internal structure of the cell observation chamber 30 in detail.

In the center of the bottom part 31a of the bottom support body 31, there is provided a window 31c for observing the movement of cells. Also, the transparent glass substrate 8 is placed on the bottom surface of the body. When the intermediate support body 32 is attached to the bottom support body 31, the glass substrate 8 is pressed firmly against and fixed to the bottom part 31a by the bottom part 32a of the intermediate support body 32. Between the bottom part 32a and the glass substrate 8 and on the outer peripheral side thereof, there is interposed an O-ring 43 to prevent medium from leaking from an inner space to be formed therebetween.

The substrate 7 is placed on the surface in the central part of the glass substrate 8. The glass substrate 8 and the substrate 7 are identical with the foregoing glass substrate 8 and substrate 7 in FIG. 1 having basically the same structure. Therefore, on the surface of the substrate 7 facing the glass substrate 8, there are engraved six units of concavo-convex shapes obtained by transferring the inner shape of the pair of wells 2A and 2B and the flow path 1 for communicating of the wells thereto, and in a state where the shapes are arranged to face and overlap the glass substrate 8, six units of combination structures of the wells 2A and 2B and the flow path 1 are formed between the substrates 7 and 8.

In the substrate 7, the through holes 3' for guiding cell suspension or chemotactic factor containing solution therethrough are also formed correspondingly to the respective wells 2A and 2B in a vertically penetrating manner, and the through holes 4' for reducing pressure increase or pressure reduction that occurs when injecting or removing the solutions into/from the wells 2A and 2B are formed in pairs with the respective through holes 3' in a vertically penetrating manner. These pairs of through holes 3' and 4' are communicated with each other through the well 2A or 2B.

The opening portion 32c is formed in the central part of the bottom part 32a of the intermediate support body 32, and the packing member 44 having a thickness slightly greater than that of the bottom part 32a is fitted into the opening portion 32c in such a manner as to protrude therefrom to press the substrate 7 placed on the glass substrate 8 from above against the glass substrate 8. The substrate 7, which has a very small thickness, is represented as a heavy solid line segment sandwiched between the glass substrate 8 and the packing member 44 in FIGS. 11 and 12. The shape of the through holes 3' and 4', the wells 2A and 2B, and the flow path 1 formed in the substrate 7 is not shown in these figures.

In the packing member 44, there are formed the same number of through holes 3-1 and 4-1 that communicate, respectively, with the through holes 3' and 4' formed in the substrate 7 in a penetrating manner as the total number of the through holes 3' and 4' in a vertically penetrating manner. Since the through holes 3' and 4' are formed in each of the wells 2A and 2B in a pair, a total of four through holes are to be formed in one unit, and integrating six units causes a total of 24 through holes (groups of through holes 3-1 and 4-1) to be formed and aligned lengthwise and crosswise. The through holes 3-1, which exist deeply and on the near side in the direction perpendicular to the space in FIG. 11, are not shown in the figure.

It is noted that the through holes 3-1 and 4-1 to be formed in the packing member 44 in a penetrating manner are not necessarily formed separately, and the through holes 3-1 may be combined with the respective through holes 4-1. This cannot cause, for example, falling solution and rising gas to be intermingled with each other, and since the gas passes through the falling solution to be discharged through a through hole 4-2 above, there is no interference with the function of reducing pressure increase in the wells. In FIG. 12 is shown the structure of thus arranged packing member 44. Also, for that purpose, if the lower end portions of through holes 3-2 and 4-2 to be formed in the cover block body 33 are cut off by a small length to form small blank spaces therein, it is possible to retain the function of reducing pressure increase and pressure reduction further reliably (refer to the two left and right small blank spaces directly below the through holes 3-2 and 4-2 in FIG. 12).

When the cover block body 33 is attached to the bottom support body 31, the lower surface of the bottom part 33$a$ of the cover block body 33 is brought into contact with the upper surface of the packing member 44 and presses the surface. Therefore, the substrate 7 is consequently to be pressed by the cover block body 33 through the packing member 44 to be fixed onto the glass substrate 8.

In one part nearer the peripheral edge of the bottom part 33$a$ of the cover block body 33, there is formed a relatively large-diameter through hole 33$d$ in a vertically penetrating manner through which mixture in the chamber 30 is adapted to go in and out of the central recessed portion 33$c$. Also, in the central part of the bottom part 33$a$, there are formed the same number of through holes 3-2 and 4-2 that communicate, respectively, with the through holes 3-1 and 4-1 formed in the packing member 44 in a penetrating manner as the total number of the through holes 3-1 and 4-1 in a vertically penetrating manner. Among these groups of through holes formed in the central part of the bottom part 33$a$, six units of the through holes 4-2 belonging to the well 2A side, that is, six aligned through holes 4-2 belonging to the well 2A side correspond one-on-one to the six through holes 34$c$ in the guide block body 34 that is attached to the cover block body 33 in the posture as shown in FIG. 8 to share the centerline thereof.

When the guide block body 34 is rotated by 180 degrees from the posture as shown in FIG. 8 to switch the positions of the arm parts 34$b$ and 34$b$ on either side with each other, six aligned through holes 4-2 belonging to the well 2B side then correspond one-on-one to the six through holes 34$c$ in the guide block body 34. Thus switching the posture of the guide block body 34 can be employed when the injection of the cell suspension into the well 2A using a micropipette is followed by the injection of the chemotactic factor containing solution into the well 2B using a micropipette.

As is clear from the description above, the through holes 3' and 4' formed in the substrate 7 in a penetrating manner, the through holes 3-1 and 4-1 formed in the packing member 44 in a penetrating manner, and the through holes 3-2 and 4-2 formed in the bottom part 33$a$ of the cover block body 33 in a penetrating manner are communicated with each other, and six units of through hole assemblies that are formed by the through holes 4', 4-1, and 4-2 thus communicating with each other correspond one-on-one to the six through holes 34$c$ formed in the guide block body 34 that is attached to the cover block body 33 in the posture as shown in FIG. 8 to share the centerline thereof (refer to FIGS. 11 and 12). It is noted that the through holes 3' and 4' formed in the substrate 7 in a penetrating manner, which have very small sizes, are not shown in FIGS. 11 and 12. The through hole assemblies composed of the through holes 4-1 and 4-2 correspond to the through holes 4 in FIG. 1.

Accordingly, assuming here that the wells 2A and 2B and the flow path 1 are filled with cell isotonic solution and that the well 2B is provided with chemotactic factor containing solution, when trying to inject cell suspension into the well 2A using a micropipette, after the needlepoint of the micropipette is inserted into one of the through holes 34$c$ that communicates with the well 2A in a unit to be used and is carried while being guided by the hole until reaching a required depth to discharge the cell suspension there, the discharged cell suspension then falls down through the through holes 4-2, 4-1, and 4' in this order to reach the well 2A. In this case, the pressure increase in the well 2A can be released outside through the through holes 3', 3-1, and 3-2, which can minimize the impact of pressure fluctuation on the chemotaxis of cells that are to react with the chemotactic factor containing solution.

The same procedure applies also when trying to inject the chemotactic factor containing solution into the well 2B using a micropipette, and in this case, the chemotactic factor containing solution discharged from the micropipette can fall down through the through holes 4-2, 4-1, and 4' belonging to the well 2B side in this order to reach the well 2B.

It is noted that it is also possible to use the through holes 3-2, 3-1, and 3' as channels for solution provision, while the through holes 4', 4-1, and 4-2 as channels for pressure reduction.

Cells in the cell suspension provided to the well 2A move from the well 2A to 2B through the flow path 1 after reacting with the chemotactic factor containing solution in the well 2B. It is possible to observe the state and measure the number of cells at the cell level through the window 31$c$ using the microscope.

In order to thus perform the operation of, for example, detecting the chemotaxis of the cells that move from the well 2A to 2B through the flow path 1 and isolating the cells utilizing the characteristics thereof, it is necessary to control the temperature of the mixture filling these sections so as to be suitable for the activity of the cells. Also when it is demanded that the reaction of the cells due to temperature change be measured and analyzed more precisely, it is necessary to control the temperature of the mixture. It is noted that the mixture filling these sections here means the mixture of the cell isotonic solution and the cell suspension and the mixture of the cell isotonic solution and the chemotactic factor containing solution, where the both mixture has approximately the same temperature.

Figure 15:
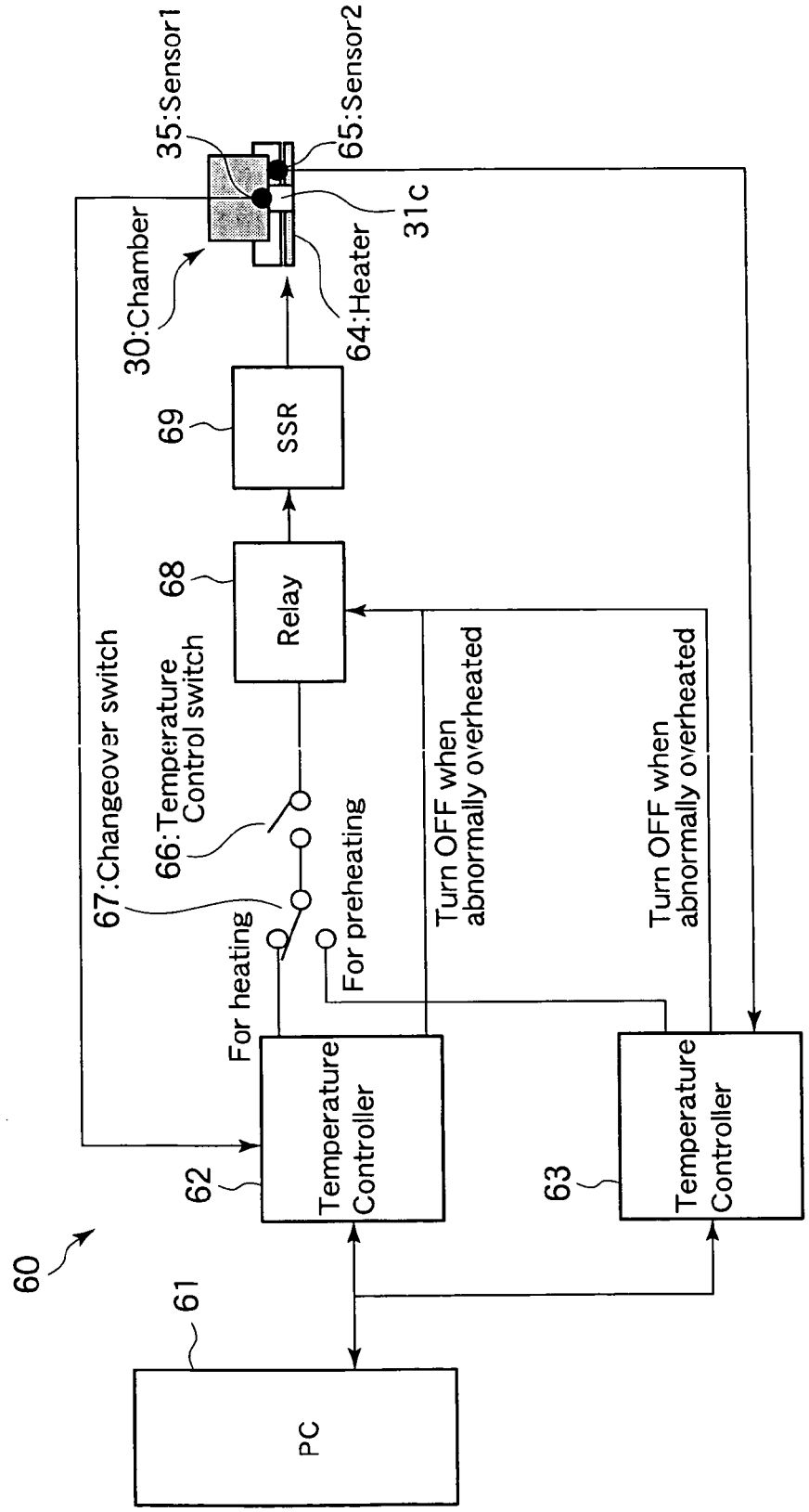
FIG. 15 is a block diagram of an in-chamber mixture temperature control system according to an embodiment of the present disclosure.

For the foregoing purpose, the present embodiment employs two temperature controllers 62 and 63 as shown in FIG. 15, where the first temperature controller 62 is adapted to use the temperature sensor 35 to measure the temperature of the mixture directly and to control the temperature of a heating section 64 to be heated by a heater with the chamber 30 being set thereon to increase the accuracy of the temperature control. Also, the second temperature controller 63 is adapted to heat the heating section 64 preliminarily so that the time required to control the temperature of the mixture to be a desired temperature can be shortened. The temperature controller 63 also has a function of preventing the heating section 64 from being overheated.

In order to measure the temperature of the mixture directly using the temperature sensor 35, a temperature sensing part 35b of the temperature sensor 35 extends downward from the pedestal part 35a, as shown in FIG. 12, to be directly sunk into a liquid storage chamber 45 filled with solution equivalent to the mixture. The solution in the liquid storage chamber 45 can receive the indirect heating by the heating section 64 equally with the solutions filling the pair of wells 2A and 2B and the flow path 1 to increase the temperature to be the same as that of the solutions, whereby the temperature sensor 35 can measure approximately the same temperature as that of the solutions filling the pair of wells 2A and 2B and the flow path 1. The liquid level of the solution in the liquid storage chamber 45 is approximately the same as the liquid level L of the mixture filling the central recessed portion 33c of the cover block body 33.

The liquid storage chamber 45 is formed with a recessed portion formed by partially and vertically chipping the outer peripheral wall of the body part of the cover block body 33 being surrounded by the inner peripheral wall of the intermediate support body 32. It is preferable that the liquid storage chamber 45 be provided separately from the wells 2A and 2B, the flow path 1, and the sections communicating with these portions. For this reason, there is interposed a packing (not shown in the figures) at the lower part of the liquid storage chamber 45 where the liquid storage chamber 45 is connected to the wells 2A and 2B, the flow path 1, and the sections communicating with these portions. This allows the temperature sensing part 35b of the first temperature controller 62 to measure the temperature of the solutions containing cells and filling the pair of wells 2A and 2B and the flow path 1 precisely without contaminating the solutions.

To describe the in-chamber mixture temperature control system 60 in more detail with reference to the block diagram shown in FIG. 15, when a temperature control switch 66 is first turned ON and a changeover switch 67 is turned ON for preheating, a preheating operation for the heating section 64 is started under the control of the temperature controller 63. The preheating operation is to be performed while measuring the temperature of the heating section 64 using a sensor 65 and feeding back the measured value. The preheating temperature is to be specified by a computer 61. The computer 61 is incorporated in the laptop computer 50. The numeral 69 indicates a solid-state relay (SSR).

When the temperature of the heating section 64 reaches a predetermined preheating temperature and the cell observation chamber 30 is placed on the heating section 64, the changeover switch 67 is turned ON for heating to start a heating operation for the heating section 64 under the control of the temperature controller 62. This heating operation, which is aiming at heating the mixture in the chamber to be a predetermined temperature, is to be performed while measuring the temperature of the mixture in the chamber using the sensor 35 and feeding back the measured value. The heating temperature is to be specified by the computer 61. Since the heating section 64 has been heated to be the predetermined temperature through the foregoing preheating operation, this heating operation can heat the mixture in the chamber to be the predetermined temperature in a short time.

When the temperature of the mixture in the chamber reaches the predetermined temperature, the temperature controller 62 performs heating control for the heating section 64 to keep the temperature. If the temperature of the heating section 64 increases abnormally (e.g. 43° C.) for some reasons, for example, that the chamber 30 is not in contact with the heating section 64, the temperature controller 63 operates the relay 68 to shut off the circuit. It is noted that the temperature controller 62 is also adapted to operate the relay 68 to shut off the circuit if the temperature of the mixture in the chamber increases abnormally (e.g. 38 to 40° C.).

The computer 61 is adapted to monitor and display the temperature of the heating section 64 and the mixture in the chamber, the state of the sensors 35 and 65, etc. constantly, and to specify a heating temperature and a preheating temperature, respectively, for the temperature controllers 62 and 63.

Here will be described in detail an actual procedure for assembling the cell observation chamber 30 according to the present embodiment.

The glass substrate 8 is first attached to the bottom support body 31. Then, the intermediate support body 32 is fitted into the bottom support body 31, and the cam control lever 37 is rotated to bring the intermediate support body 32 into pressurized contact with the bottom support body 31 from above through the O-ring 43 and to attach the intermediate support body 32 to the bottom support body 31. This can prevent medium from leaking to give the assembly composed of these components a function as a container. Next, the substrate 7 is placed on the glass substrate 8 while being guided by the opening portion 32c formed in the central part of the bottom part 32a of the intermediate support body 32, and the cover block body 33 with the packing member 44 attached to the bottom surface thereof is fitted into the intermediate support body 32, and then the cam control lever 36 is rotated to bring the packing member 44 into pressurized contact with the substrate 7 from above and to bring the substrate 7 into pressurized contact with the glass substrate 8. At the same time, the cover block body 33 is brought into pressurized contact with the intermediate support body 32 through the O-ring 42 to be attached to the bottom support body 31. This can prevent the medium from leaking to give the general assembly (cell observation chamber 30) composed of these components also a function as a container.

Next will be described the internal structure of the cell observation apparatus 10 according to the present embodiment shown in FIGS. 16 and 17.

Figure 16:
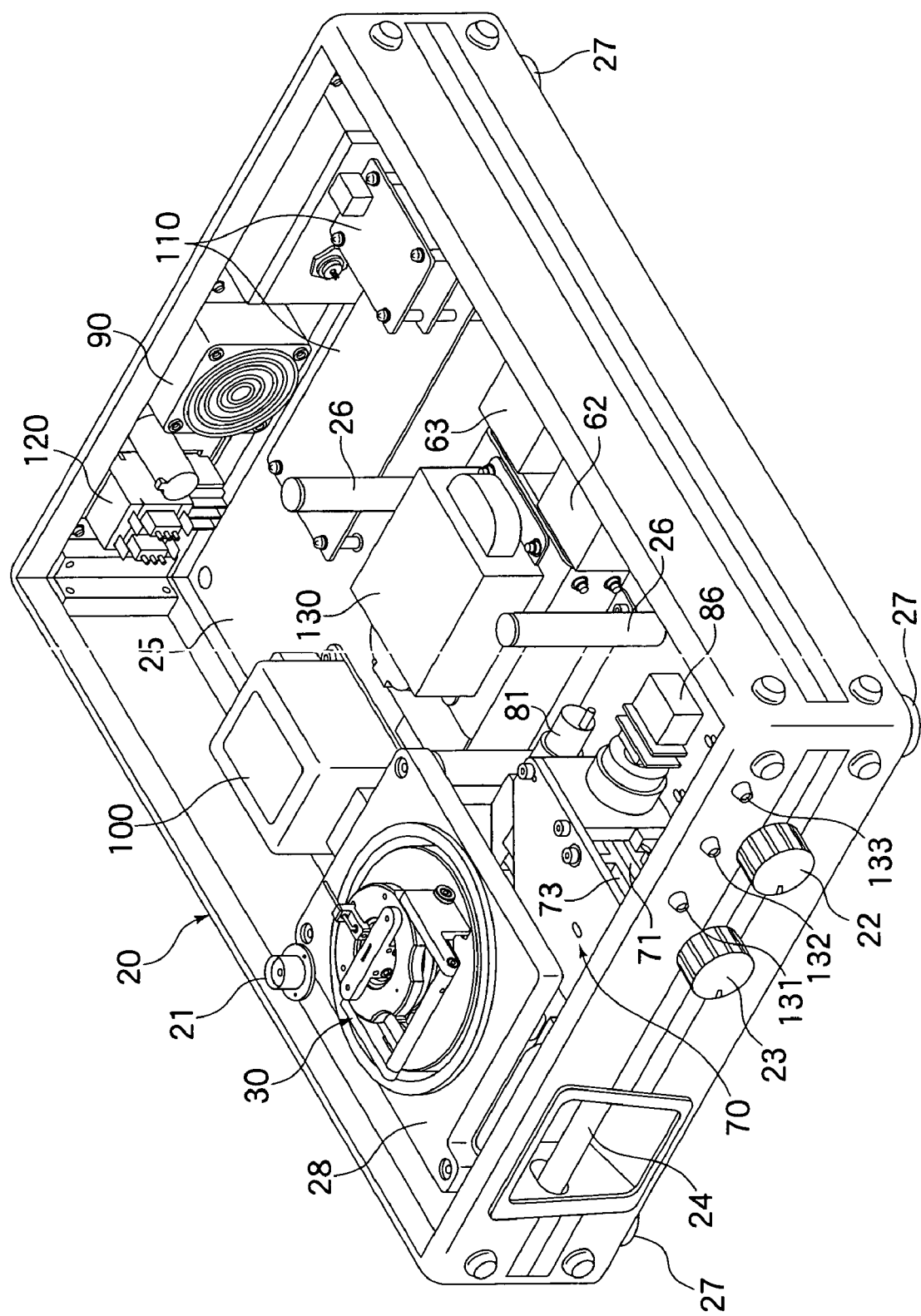
FIG. 16 is a perspective view inside a casing of a cell observation apparatus according to an embodiment of the present disclosure.
Figure 17:
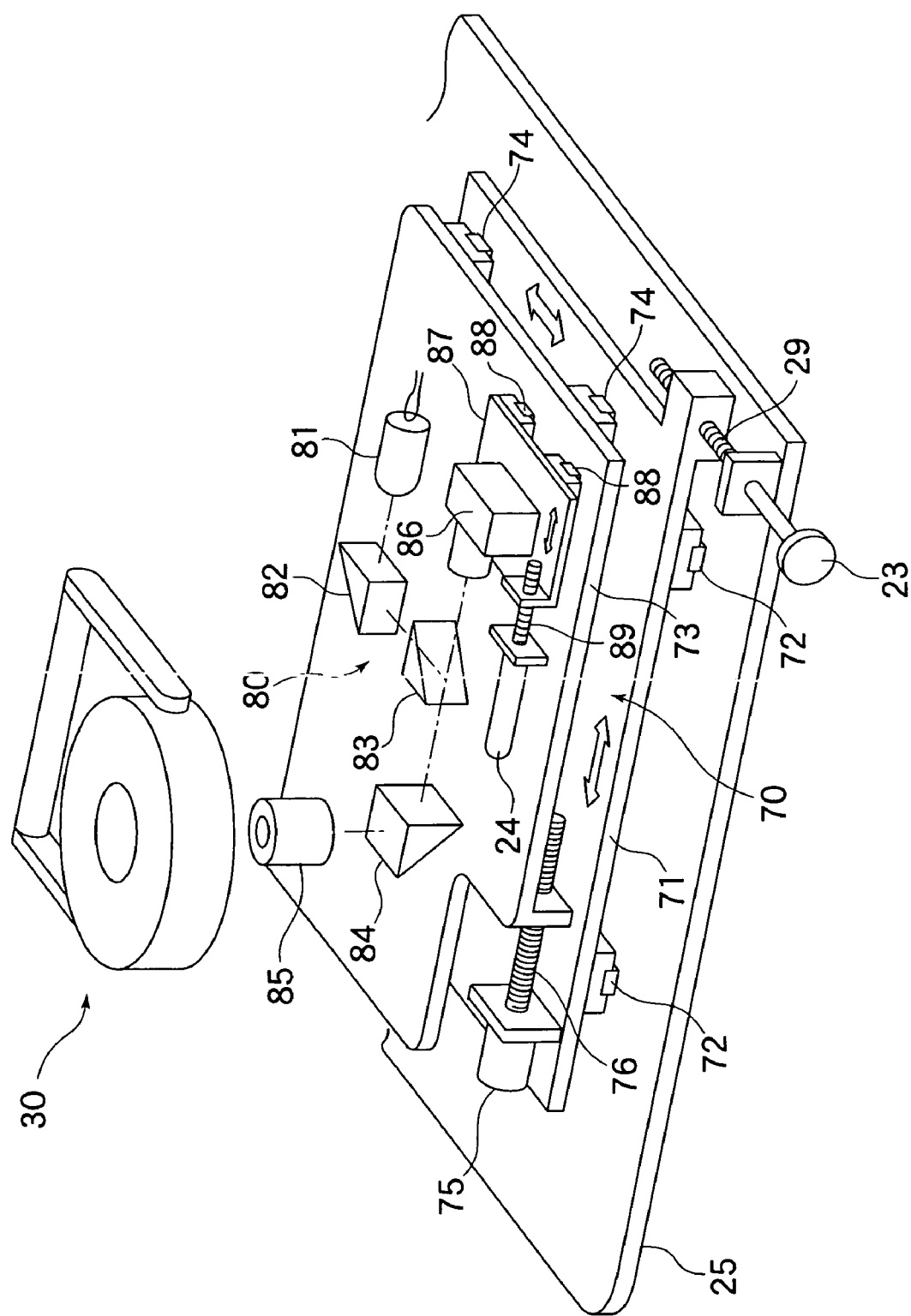
FIG. 17 is a schematic view of an optical observation means.

FIG. 16 is a perspective view in the casing 20 of the cell observation apparatus 10 according to the present embodiment, and FIG. 17 is a view typically showing the schematic configuration of the optical observation means.

As mentioned above, the cell observation chamber 30 is housed nearer a corner in the casing 20 of the cell observation apparatus 10 according to the present embodiment in such a manner that a part (part of the side of providing or removing solutions) of the cell observation chamber 30 is exposed from the upper surface of the casing 20. The cell observation chamber 30 is set in such a manner as to be sunk into a central recessed portion of an installation mount 28 that is installed in the casing 20 so that the cell observation chamber 30 can be replaced easily as appropriate.

The optical observation means 70 is provided below the cell observation chamber 30. As shown in FIG. 17, the optical observation means 70 comprises an optical system 80 on a stage movable in an XY two-dimensional plane, the system consisting of an objective lens 85; two reflecting mirrors 82 and 84; a half mirror 83 arranged between the reflecting mirrors 82 and 84; a light source 81; and a CCD camera 86, and the optical axis thereof indicated by the alternate long and short dash line extends horizontally though inflected partially except that the axis runs vertically through a small distance where light passes through the objective lens 85. The optical system 80 has a structure achieved by combining the microscope with the CCD camera 86.

The objective lens 85 is arranged near and under the window 31c provided in the center of the bottom part 31a of the bottom support body 31 in the cell observation chamber 30 so that cells moving through the flow path 1 for communicating of the pair of wells 2A and 2B can be observed.

Light generated from the light source 81 is to be reflected by the reflecting mirror 82, half mirror 83, and reflecting mirror 84 in this order to enter and pass through the objective lens 85 to illuminate the cells in the flow path 1. The image of thus illuminated cells is to be magnified to a predetermined size by the objective lens 85 to enter the reflecting mirror 84 and be reflected thereat to enter the half mirror 83. Then, the camera 86 acquires the image after passing through the half mirror straightforward to take a visible image. The light intensity of the light source 81 can be adjusted by operating the brightness adjustment knob 22.

The camera 86 is fixed on a mounting 87, the mounting 87 being installed on a second stage 73 to be described hereinafter in such a manner as to be slidable along a linear guide 88. Then, operating the focal point adjustment knob 24 allows the mounting to be slid in the direction toward the half mirror 83 through a screw connection between a screw rod 89 linked to the focal point adjustment knob 24 and the mounting 87, so that the focal point of the camera 86 is to be adjusted.

The image of the cells taken by the camera 86 is to be converted into digital data and sent to the personal computer 50 to be held and memorized therein, and to be displayed on the display of the personal computer 50 as appropriate. The objective lens 85 is to be replaced to change the magnified size of the image of the cells. The image can also be magnified or demagnified using a zoom function incorporated in the personal computer 50. It is thus possible to observe the state of the cells moving from the well 2A to the well 2B through the flow path 1 and to measure the number of the cells at the cell level.

The stage movable in the XY two-dimensional plane, which forms the base of the optical observation means 70, is arranged as follows.

As shown in FIG. 17, the stage is composed of two stages: a first stage 71 and a second stage 73. The first stage 71 is provided on the bottom plate 25 of the casing 20 in such a manner as to be slidable in the X direction along a linear guide 72 with respect to the bottom plate 25. It is here noted that the X direction indicates the direction perpendicular to the optical axis that links the camera 86 and the reflecting mirror 84. The first stage 71 can be slid in the X direction by operating the position adjustment knob 23 through a screw connection between a screw rod 29 integrated with the position adjustment knob 23 and the first stage 71.

Also, the second stage 73 is provided on the first stage 71 in such a manner as to be sidable in the Y direction (perpendicular to the X direction) along a linear guide 74 with respect to the first stage 71. The second stage 73 can be slid in the Y direction by operating a motor (stepping motor) 75 through a screw connection between a screw rod 76 integrated with the rotation axis of the motor 75 and the second stage 73. The motor 75 can be controlled through the personal computer 50.

It is noted that although the light intensity, stage position, and focal point are adjusted, respectively, by the brightness adjustment knob 22, position adjustment knob 23, and focal point adjustment knob 24, each adjusting function may be incorporated in a program of the personal computer to make each adjustment through a program switch or a switch key attached to the personal computer. Also, each operating function may be operated by an automatic startup device such as a motor or may be adjusted manually through adjustment knobs provided in the respective parts to be adjusted.

In the casing 20, there are also housed, for example, the first temperature controller 62 and the second temperature controller 63 as components in the in-chamber mixture temperature control system 60, a fan 90, a noise filter 100, a control circuit section 110, a connector 120 for connection of various wirings, and a power supply section 130.

Among these components, the temperature control system 60 functions as means (temperature control means) for controlling the solutions (mixture) filling the pair of wells 2A and 2B and the flow path 1 to be a predetermined temperature as mentioned above. The fan 90 is adapted to keep the atmospheric temperature in the casing 20 as evenly as possible by taking and distributing the external air into the casing 20 evenly and then discharging the air. The control circuit section 110 is connected to the personal computer 50 through the connector 120.

In the casing 20, there may be further provided means (temperature control means) for controlling the atmosphere in the casing 20 to be a predetermined temperature, though not shown in the figure. This means has a heater, an atmospheric temperature measuring sensor, and a temperature controller, and is connected to the personal computer 50 to heat or cool the atmosphere in the casing 20 so that the casing 20 can also be filled with an atmosphere having a uniform temperature. This can further ease the impact of external temperature change on the mixture in the chamber 30 to keep the mixture at a predetermined temperature.

The lower surface of the casing 20 is fitted with the tilt adjustment means 27 for adjusting the tilt of the casing 20 in the four corner portions. Since the tilt adjustment means 27 are formed by threadably fitting the screw portions of shouldered bolts into female thread portions that are formed, respectively, in the four corner portions on the lower surface of the casing 20, when it is found by the level 21 that the casing 20 is out of the horizontal position, it is possible to restore the evenness by rotating tilt adjustment means 27 provided in any corner portion corresponding to the corner out of the horizontal position. Also, the impact of the gravity on the chemotaxis of cells can be observed, if demanded, by rotating the corresponding tilt adjustment means 27 by a predetermined amount to incline the casing 20 by a predetermined angle.

A power indicator 131 is provided in the upper right portion on the front surface of the casing 20 so that the state where the power supply section 130 is turned on or off is to be indicated. There are also provided alarm lamps 132 and 133. The alarm lamp 132 is adapted to be turned on in the event of a heating system failure. For example, the alarm lamp is to be turned on when the temperature of a heating plate increases higher than a preset temperature of a thermostat (e.g. 52° C.). Also, the alarm lamp 133 is adapted to be turned on, for example, when the temperature becomes still higher (e.g. 90° C.) with the alarm lamp 132 being turned on.

On the bottom plate 25 of the casing 20, there are disposed a plurality of support pillars 26 for supporting the cover plate of the casing 20 in places.

The cell observation apparatus 10 according to the present embodiment, which is thus arranged, can exhibit the following effects.

Since the optical observation means 70 is housed in the casing 20 below the cell observation chamber 30 in such a manner that the optical axis thereof extends horizontally, the overall height of the casing 20 can be saved considerably, which can reduce the size and weight of the cell observation apparatus 10 to be movable easily. Also, the apparatus can be operated easily, resulting in a significant improvement in operationality.

Also, the optical observation means 70 can move and align the objective lens 85 to a position under the flow path 1 through which cells to be observed move and can magnify the cells, so that the camera 86 can take a visible image of the cells and that a state where the cells move can be observed and the number of the cells can be measured using the image, which facilitates the cell observing operation significantly. Since there is also provided the half mirror 83, it is possible to change the angle of the optical axis randomly by arranging the half mirror between the reflecting mirror 84 and the camera 86 as well as between the reflecting mirror 84 and the reflecting mirror 82, which can further reduce the size of the cell observation apparatus 10.

In addition, since the cell observation apparatus 10 comprises the temperature control means to control the solutions (mixture) filling the pair of wells 2A and 2B and the flow path 1 and the atmosphere in the casing 20 to be a predetermined temperature, it is possible to detect the chemotaxis of cells precisely at the temperature suitable for the activity of the cells, which allows the impact of temperature on the chemotaxis of the cells to be measured and analyzed precisely. Further, the temperature change of each part housed in the casing 20 and constituting the cell observation apparatus 10 can have a regular impact on the chemotaxis of the cells, and thus the accuracy and depth in observing the cells can be improved.

In particular, the temperature control means (temperature control system 60) for controlling the solutions filling the pair of wells 2A and 2B and the flow path 1 to be a predetermined temperature is adapted to measure the temperature of the solutions directly to control the solutions to be the predetermined temperature, which can further improve the accuracy in observing the cells.

Further, since it is arranged that on the upper surface of the casing 20 can be placed the personal computer 50 capable of holding a program for temperature control in the temperature control means and cell observation data, etc., processing the data, and displaying desired data on a display, a series of cell observing operations such as operating the cell observation apparatus 10, observing the state of cell, and holding, processing, and analyzing data can be facilitated significantly and also the operations can be performed on a desk. Also, the space for installing the personal computer 50 can be saved, and the computer can be moved integrally with the cell observation apparatus 10 to be movable easily.

Furthermore, since the lower surface of the casing 20 is fitted with the tilt adjustment means 27 for adjusting the tilt of the casing 20, the gravity can have a regular impact on the chemotaxis of cells, and additionally the impact of the gravity on the chemotaxis of the cells can be measured and analyzed precisely.

It is noted that the present invention is not restricted to the above-described embodiment, and various modifications may be made without departing from the gist thereof.

What is claimed is:

1. A cell observation apparatus comprising:
   a cell observation chamber comprising therein a pair of wells and a flow path for communication between said wells and being arranged in such a manner that cells in cell suspension stored in one of said wells can react with chemotactic factor containing solution stored in the other of said wells to move from one to the other of said wells through said flow path and a window, in a bottom portion of said cell observation chamber, for observing the movement of cells:
   optical observation means for observing said cells moving through said flow path optically from outside said cell observation chamber, said optical observation means comprising a camera, an objective lens arranged vertically upward on a vertical axis, an optical axis extending horizontally between said camera and said vertical axis of said objective lens and a light source illuminating, through said window, said cells moving through said flow path;
   a casing housing said optical observation means, said optical observation means being housed in a main body of said casing below said cell observation chamber with said objective lens near and below said window; and
   an XY stage comprising a first stage mounted within the casing for sliding movement in an X direction and a second stage mounted on the first stage for movement relative to the first stage in a Y direction perpendicular to the X direction, wherein said optical observation means includes an optical system mounted on said second stage and wherein said camera is slidably mounted on said second stage for sliding horizontal movement relative to said second stage.

2. The cell observation apparatus according to claim 1, wherein:
   said optical system comprises said objective lens, a plurality of reflecting mirrors, a half mirror, said light source, and said camera, and
   said light source generates light which illuminates, through said objective lens and through said window, said cells moving through said flow path, to allow said camera to image said cells illuminated by said light.

3. The cell observation apparatus according to claim 1, further comprising temperature control means for controlling the temperature of the atmosphere in said casing and the main body of said casing to be a predetermined temperature.

4. The cell observation apparatus according to claim 1 wherein
   said X direction is perpendicular to said optical axis; and
   said sliding horizontal movement of said camera is along said optical axis.

5. The cell observation apparatus according to claim 2, further comprising temperature control means for controlling the temperature of the atmosphere in said casing and the main body of said casing to be a predetermined temperature.

6. The cell observation apparatus according to claim 2 wherein
   said X direction is perpendicular to said optical axis; and
   said sliding horizontal movement of said camera is along said optical axis.

* * * * *